United States Patent [19]

Luppi

[11] 4,440,722
[45] Apr. 3, 1984

[54] DEVICE FOR OXYGENATING BLOOD CIRCULATING IN AN EXTRACORPOREAL CIRCUIT WITH A HEAT EXCHANGER

[75] Inventor: Libero Luppi, Mirandola, Italy

[73] Assignee: Dideco S.p.A, Mirandola, Italy

[21] Appl. No.: 308,322

[22] Filed: Oct. 2, 1981

[30] Foreign Application Priority Data

Oct. 6, 1980 [IT] Italy ............................ 25141 A/80
Jul. 10, 1981 [IT] Italy ............................ 22864 A/81

[51] Int. Cl.³ .................................................. A61M 1/03
[52] U.S. Cl. ............................. 422/46; 128/DIG. 3; 261/DIG. 28; 422/47
[58] Field of Search ............ 422/46, 47; 128/DIG. 3; 261/DIG. 28

[56] References Cited

U.S. PATENT DOCUMENTS

| | | | |
|---|---|---|---|
| 2,652,831 | 9/1953 | Chesler | 422/47 |
| 3,729,377 | 4/1973 | Leonard | 422/47 X |
| 3,827,860 | 8/1974 | Burlis | 422/47 |
| 3,994,609 | 11/1976 | DeWall | 422/46 |
| 4,138,288 | 2/1979 | Lewin | 422/46 X |
| 4,140,635 | 2/1979 | Esmond | 422/47 X |
| 4,158,693 | 6/1979 | Reed et al. | 422/47 X |
| 4,205,042 | 5/1980 | Lobdell et al. | 422/46 X |
| 4,256,692 | 3/1981 | Cover | 422/46 |
| 4,280,981 | 7/1981 | Harnsberger | 422/47 X |

*Primary Examiner*—Barry S. Richman
*Attorney, Agent, or Firm*—Guido Modiano; Albert Josif

[57] ABSTRACT

The device comprises plural oxygenation modules, each of which has at least one member for diffusing oxygen through the blood, and one shutter for shutting off such fluids. The modules communicate with a chamber wherethrough the pipes of a heat exchanger extend, and with a collecting chamber through a layer of an antifoaming material.

4 Claims, 4 Drawing Figures

DEVICE FOR OXYGENATING BLOOD CIRCULATING IN AN EXTRACORPOREAL CIRCUIT WITH A HEAT EXCHANGER

BACKGROUND OF THE INVENTION

This invention relates to a device for oxygenating blood circulating in an extracorporeal circuit with a heat exchanger.

It is known that in the course of some surgical procedures it becomes necessary to circulate blood externally to the patient's body. During the extracorporeal circulation blood requires to be oxygenated and heated in order to maintain the normal body temperature, or cooled where momentarily operating in hypothermia. For this purpose, devices have been proposed, known as oxygenators, which comprise a heat exchanger capable of performing the above functions. These oxygenators are not devoid of shortcomings.

It will be appreciated, first of all, that a basic requirement of an oxygenating device is that blood flows through it in optimum conditions, both from the standpoint of enabling a good intermixing of oxygen, and from that of preventing stagnation points or the throwing of blood against the walls of the device, which could have fatal results causing hemolysis phenomena, i.e. collapsing of red cells, and from the very important standpoint of minimizing contact of blood with the walls of the device, which constitute a foreign object susceptible to become a source of contamination and other complications.

The optimization of the blood flow is of course achieved with a suitable selection of the cross-section dimensions of the passageways within the oxygenator in accordance with the blood flow rate; because of the fact that this flow rate varies in a directly proportional way to the patient's weight, conventional devices are manufactured in three different sizes, one of which is intended for newly born children, one for pediatric applications, and one for adult applications, in an attempt to approach as far as possible the optimum conditions in each case; however it is evident that the optimization thus achieved can only be a coarse one because each of the three types will have to accommodate widely different flow rates both on account of the different weights of the patients being treated and because any individual patient may involve momentarily different conditions especially when the surgical operation is carried out in conditions of hypothermia, with attendant greatly reduced blood flow rate.

Moreover, the availability of three sizes of oxygenators leads to problems in respect of supplying and inventory. To the coarse optimization of the sizes of conventional oxygenating devices as a function of the blood flow rate there is connected another negative aspect. This aspect consists in that the amount of blood which must be retained within the apparatus in order to allow priming of the apparatus, does not proportionally follow flow rate drops, but is constantly disproportionately high, thus subtracting blood from the amount required by the surgeon to face contingent situations.

SUMMARY OF THE INVENTION

One object of the invention is to eliminate such prior drawbacks by providing an oxygenating device which can operate with different blood flow rates in an optimum manner, as required by different weights of patients, from newly born children to adults.

It is another object of the invention to provide an oxygenating device wherein the heat exchanger presents a large exchange surface area for any blood flow rate, thus affording short times particularly for the heating step which follows a hypothermia stage.

Another object of the invention is to provide an oxygenating device of small size and cost.

According to one aspect of the present invention the aforesaid objects are achieved by a device for oxygenating blood circulating in an extracorporeal circuit with a heat exchanger, characterized in that it comprises a plurality of oxygenating modules, each module comprising at least one diffuser for diffusing oxygen through the blood and a shutter for shutting off the two fluids, the diffuser and shutter being included in a distributor into which there open a venous blood manifold and an oxygen manifold, and an underlying chamber through which there extend the pipes of a heat exchanger, said oxygenating modules being in communication, through a layer of an antifoaming material, with an arterial blood collecting and storing chamber provided with outlet fittings.

With a device of this type, it will be apparent how, by suitably manipulating the shutters, it becomes possible to operate the most suitable number of oxygenation modules in accordance with the required flow rate, thus achieving a much sophisticated optimization of the blood flow conditions; consequently, optimum oxygenation, a continuous stagnation-free and splash-free flow, and minimal blood-to-walls contact are achieved as well as a priming action which is strictly a function of the flow rate.

BRIEF DESCRIPTION OF THE DRAWINGS

Further features and advantages will become more clearly apparent from the following description of a preferred but not limitative embodiment of the invention, as illustrated by way of example only in the accompanying drawings, where.

DESCRIPTION OF THE PREFERRED EMBODIMENT

Figure 4:
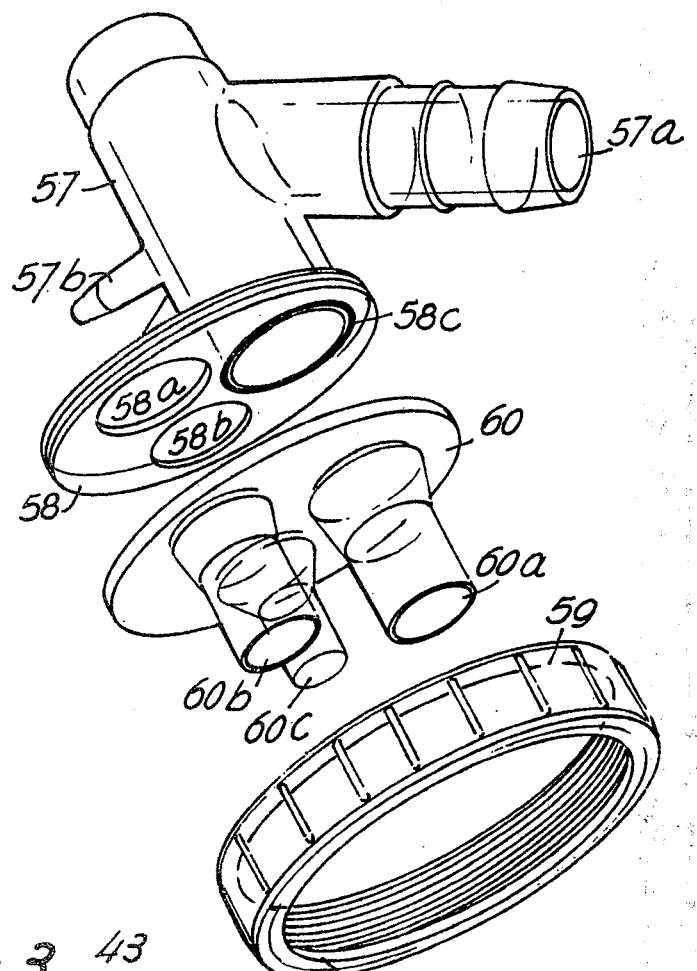
FIG. 4 is an exploded view of a venous blood inlet fitting.

With reference to a drawing figure, there is indicated at 1 the distributor to which there is delivered, through a connector or fitting 2, which will be described in detail hereinafter with reference to FIG. 4, the venous blood flowing through a venous inlet manifold 3 secured to the housing of the device. Through a fitting, oxygen flows into a manifold 5 secured to the housing of the device and defined within a cover 6 which comprises a filter 7 bearing against supporting plates 8.

Figure 1:
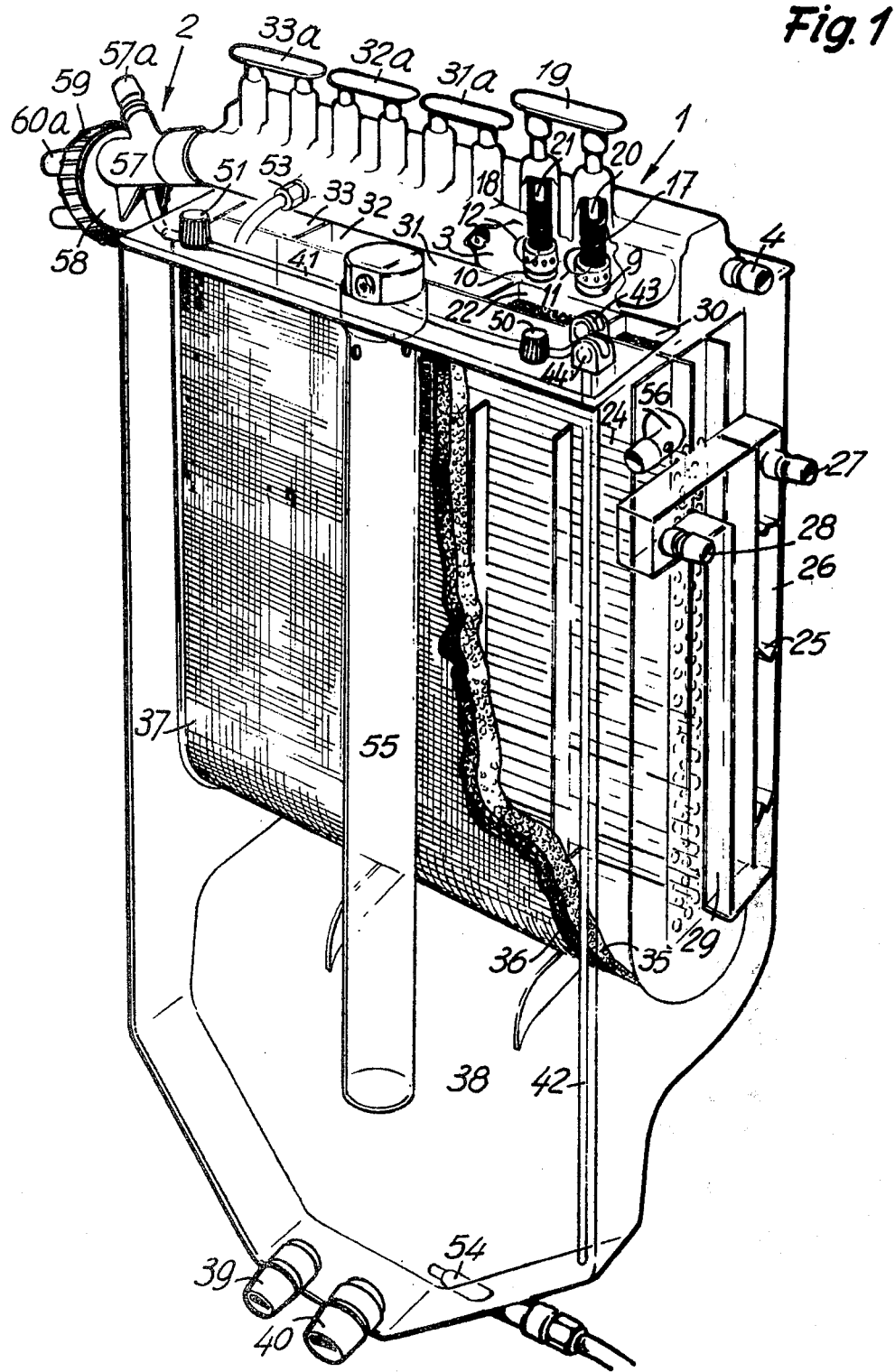
FIG. 1 is a perspective view of a device according to the invention showing some members partly cut away and in ghost lines.

An oxygenation module, shown cut away in FIG. 1 and arranged between the interior of the manifolds 3 and 5 and the interior of the housing, comprises two oxygen diffusers made up of stub pipes 9 and 10 communicating, through holes 11 and 12, with the interior of the venous blood inlet manifold 3 and having walls provided with through holes as at 13 for the stub pipe 9. Oxygen is admitted through the holes 13 to mix with blood and comes from wells 14, which communicate through holes 15 with a chamber 16 whereinto the oxygen is introduced through the filter 7.

The two stub pipes 9 and 10 are equipped with blood and oxygen shutter means comprising plungers 17 and 18 made of an elastic material, such as rubber, and being shown in the figures at their stroke bottom end in position to shut off both fluids, i.e. to shut off communication of the interior of the stub pipes 9 and 10 with the interior of the manifolds 3 and 5.

The concurrent sliding movement of the two plungers in contact with the walls of the related stub pipes and the walls of holes such as 9a for the stub pipe 9 to reach their top stroke end into a position of free admission of oxygen and blood, that is with their downward faces at a higher level than the holes 11 and 12 such as to open communication between the stub pipes 9 and 10 and the manifolds 3 and 5 is accomplished by pulling up a common operating member in form of a handle 19 which connects small metal rods 20 and 21 rigid with the plungers 17 and 18 and is operable from outside the housing of the device.

The described oxygenation module, which comprises stub pipes 9 and 10 each extending substantially perpendicularly to the manifold 3, also comprises underlying mixing chamber 22 whereinto the blood is introduced by gravity from said stub pipes to first meet a non-siliconed layer of polyurethane 23 which deadens the impact and homogenizes the blood and oxygen foam to facilitate the mixing of blood and oxygen. Subsequently the blood meets pipes 24 of a heat exchanger arranged below the homogenizing filter and adapted for conveying a flow of water, which is suitably directed by partitions, 25, and a manifold 29 through a fitting 28 and leaves the heat exchanger through a fitting 27 of the manifold 26 located at the same level as the fitting 28 to prevent the exchanger from becoming emptied; advantageously, the pipes 24 are arranged in staggered rows along directions perpendicular to the flow of blood sweeping them externally, that is the pipes 24 are horizontal in the normal operating position of the device, thereby a sort of blood lamination is produced with attendant increase of the contact area thereof with the individual oxygen bubbles.

In addition to the oxygenation module just described, the device illustrated in the figures, and particularly in FIG. 1, also comprises a module made up of a chamber 30 and overlying stub pipes, not shown, whereinto the blood and oxygen are introduced at all times during the operation because said stub pipes are not equipped with shut-off members. The device further has modules comprising chambers 31, 32 and 33 with related overlying stub pipes, not shown, shut-off members operable by manipulating handles 31a, 32a and 33a, respectively.

Figure 2:
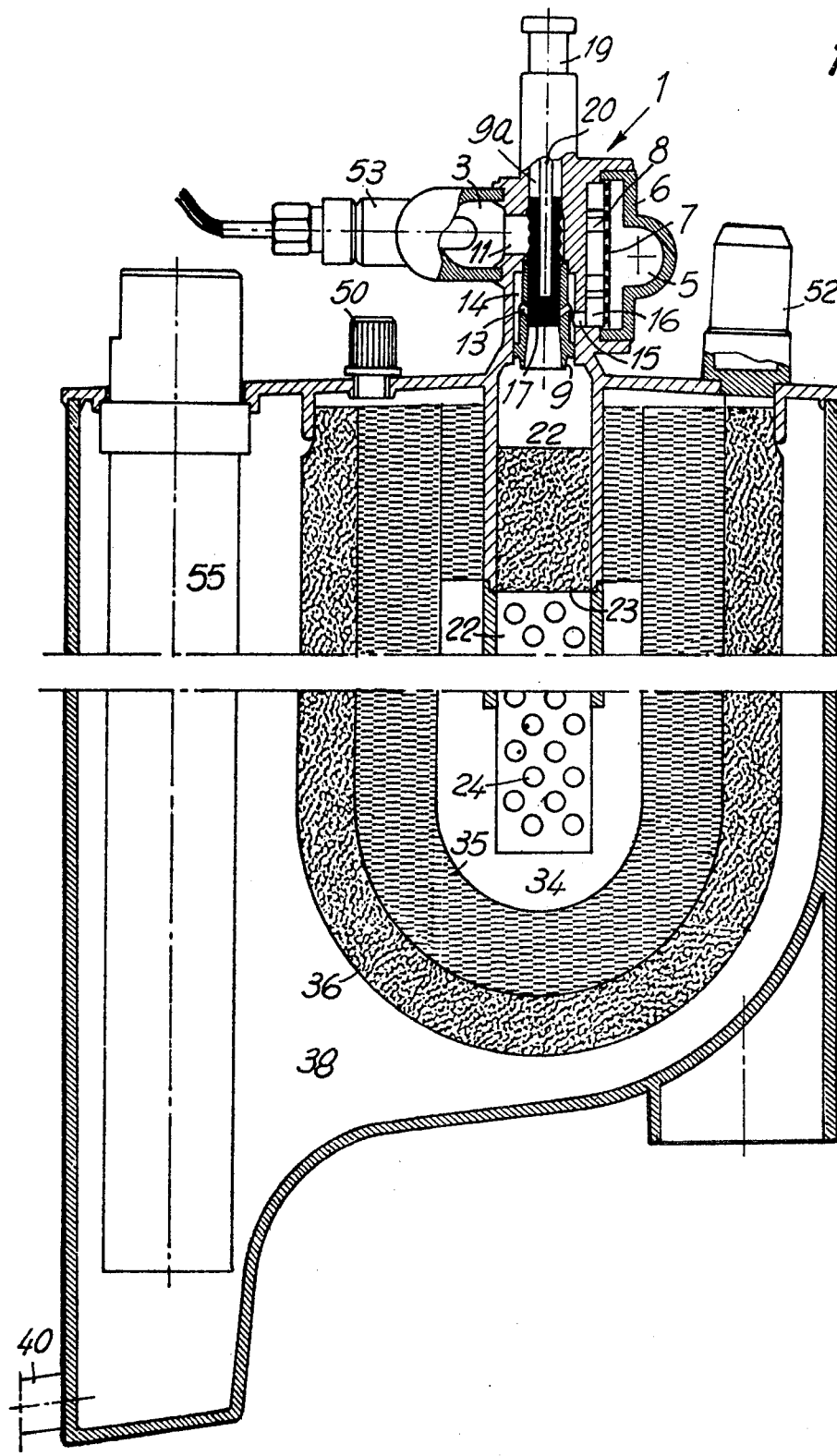
FIG. 2 shows a section, interrupted at the middle area, of said device with a cross plane including the axis of the first diffuser shown in the cut away view of FIG. 1.

The foaming blood which leaves the chambers of the modules described hereinabove reaches the space portion indicated at 34 in FIG. 2, and hence, through the layers 35 and 36 of a suitable two-grade siliconed material with antifoaming functions and through a filter screen 37, reaches a collecting and storing chamber 38 equipped with outlet fittings 39 and 40. As visible in the drawings, the antifoaming filter is arranged according to a U-like shape i.e. it has a U-like cross section generally surrounding the heat exchanger.

Figure 3:
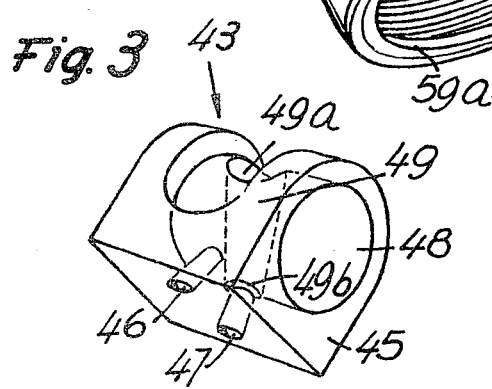
FIG. 3 is an isometric view, with members shown in ghost lines, of a withdrawal tap.

There are indicated at 41 and 42 two small pipes respectively connected to the venous blood inlet fitting 2 and arterial blood collecting chamber 38, and to the taps 43 and 44 for spilling of samples; said taps are identical, and the one indicated at 43 will be described in detail with reference to FIG. 3.

Said tap comprises a fixed body 45 having a passage 46 connected to the small pipe 41 and a passage 47 connected to the collecting chamber 38, and a rotary body 48 having the bore 49 which can be brought, by manual operation, in a position suitable for receiving a syringe inserted through an end 49a, with the opposed end 49b facing one of the two passages 46 and 47.

The withdrawal of the sample is effected by first sucking with the syringe the blood contained in the small pipe 41 through the passage 46. This blood is considered non-valid for sampling and is thus ejected, after a suitable rotation of the body 48, through the passage 47. Renewed blood in pipe 41 is then sucked through the passage 46, after having rotated back the body 48. Indicated at 50 and 51 are two fittings for the introduction of any suitable substances, while 52 indicates a fitting for quick filling, 53 and 54 indicate two probes for detecting the temperature, 55 denotes a probe for detecting the level of the blood in the chamber 38, and 56 indicates an outlet fitting provided for the gases to be removed from the device interior. Outlet fitting 56 has an anti-implosion hole.

Finally, and with reference to FIG. 4, the venous blood inlet connector 2 will be described. Said connector includes a fitting 57 connected with one end to the manifold 3 and having at its other end a flange 58, provided with bores 58a and 58b and having a gasket 58c arranged at a bore of the flange 58 aligned with the fitting 57. The flange 58 is threaded on the outer edge to match the inside threads of a ring nut 59 which has an abutment 59a for retention and compression of the disk 60 against the flange 58 and the fitting 57, said disk has three through holes and three stub pipes 60a, 60b and 60c of different diameters, the most suitable one for infant use, or pediatric, or adult applications, being positioned to correspond with the hole of the fitting 57. On said fitting 57, there are provided a branching off 57a for connection to a cardiotomy apparatus and a branch-off 57b for connection to the small pipe 41 for the withdrawal of venous blood samples.

It will be appreciated from the foregoing description how, with extremely simple manipulations, it becomes possible to determine at any time the optimum cross-section for the blood passage by admitting the same to the most suitable number of oxygenation modules, thus achieving all of the advantages described hereinabove, that is optimum admixture of oxygen, a splash-free flow with minimal contact with the walls of the device; moreover the reduction of priming to strictly indispensable amounts for each flow rate can cause the involvement of a minimal amount of antifoaming material.

Also noteworthy is the feature of the oxygen and venous blood shut-off member of each oxygenation module, which shut-off member is effective to shut off the two fluids in an almost simultaneous way, thus avoiding the problems which may result from the shutting off of just one of said fluids.

Another important aspect of the invention resides in that the heat exchanger is provided with a large width dimension, and ensures, even with the smallest flow rates, a large exchange surface, contrary to what happens in known devices where the exchangers for the infant or pediatric sizes will be of reduced dimensions.

The invention described above is susceptible to many modifications and variations without departing from the scope of the instant inventive concept; it is evident, for example, that the number of the oxygenation modules may be different from the one shown, and that for each module the number of the stub pipes may be different from the two described.

Furthermore, nothing changes in principle where the blood inlet is located at any other point with consequent variation of the flow direction.

In practicing the invention, all of the details may be replaced with other technically equivalent elements; the materials used, as well as the shapes and dimensions, may be any suitable ones for the intended application.

I claim:

1. A device for oxygenating blood circulating in an extracorporeal circuit, comprising a housing, a venous blood inlet manifold and an oxygen inlet manifold secured to said housing, a plurality of oxygenating modules each arranged between the interior of said manifolds and the interior of said housing, a blood and oxygen mixing chamber in said housing below said oxygenating modules and communicating therewith, a homogenizing filter in said mixing chamber, a heat exchanger in said housing below said homogenizing filter, an antifoaming filter generally surrounding said heat exchanger in said housing, an arterial blood collecting chamber in said housing, and arterial blood outlet fittings communicating with said arterial blood collecting chamber, wherein each of said oxygenating modules comprises at least one stub pipe extending substantially perpendicularly to said venous blood inlet manifold and directed into said mixing chamber, a shutter means for controlling communication between the interior of said at least one stub pipe and the interior of said venous blood inlet manifold, inclined through holes in said at least one stub pipe for providing communication between the interior of said at least one stub pipe and the interior of said oxygen inlet manifold, and wherein said shutter means comprises a plunger of elastic material slidable in contact with said at least one stub pipe inside thereof between a position in which communication of said at least one stub pipe with said manifolds is closed and a position in which the latter communication is open, and wherein plungers of stub pipes of a same oxygenating module have a common operating member operable from outside said housing for selectively operating said oxygenating modules thereby adapting the device to different blood flow rates while maintaining substantially a constant degree of oxygenation of the blood flowing through the device.

2. A device as claimed in claim 1, wherein said plungers are each rigid with respective metal rods, and said operating member comprises a handle connecting the metal rods of the plungers of a same oxygenating module.

3. A device as claimed in claim 1, wherein said heat exchanger has water conveying pipes extending perpendicularly to the flow direction of oxygenated blood from said mixing chamber to said antifoaming filter, said antifoaming filter having a U-like cross section.

4. A device as claimed in claim 1, further comprising a fitting connected to said blood inlet manifold, a flange having three bores of different size, a disc having three through holes and three stub pipes corresponding to said three bores, said flange and disc being secured to said fitting such that communication to said venous blood inlet manifold is provided selectively through one of said three bores, through holes and stub pipes.

* * * * *